(12) United States Patent
Schal et al.

(10) Patent No.: US 6,992,230 B2
(45) Date of Patent: Jan. 31, 2006

(54) PROCESS FOR THE PRODUCTION OF 1,5-DINITRONAPHTHALENE

(75) Inventors: Hans-Peter Schal, Dormagen (DE); Vera Yakovlevna Popkova, Moskau (RU); Boris Mikhaylovitch Laskin, St. Petersburg (RU); Alexander Sergeevitch Malin, St. Petersburg (RU); Sofia Borisovna Volkova, St. Petersburg (RU)

(73) Assignee: Bayer MaterialScience AG, Leverkusen (DE)

( * ) Notice: Subject to any disclaimer, the term of this patent is extended or adjusted under 35 U.S.C. 154(b) by 0 days.

(21) Appl. No.: 10/979,949

(22) Filed: Nov. 2, 2004

(65) Prior Publication Data

US 2005/0107646 A1    May 19, 2005

(30) Foreign Application Priority Data

Nov. 5, 2003    (EP) ................................. 03025412

(51) Int. Cl.
*C07C 205/00*    (2006.01)

(52) U.S. Cl. ........................ 568/931; 568/928; 568/930

(58) Field of Classification Search ................ 568/928, 568/930, 931
See application file for complete search history.

(56) References Cited

U.S. PATENT DOCUMENTS

| 3,221,062 A | 11/1965 | Wright ........................ 260/622 |
| 3,998,893 A | 12/1976 | Dürholz et al. .............. 260/645 |
| 6,242,656 B1 | 6/2001 | Steinlein et al. ............ 568/930 |
| 6,420,616 B1 | 7/2002 | Gürtler et al. .............. 568/931 |

FOREIGN PATENT DOCUMENTS

| DE | 26541 | 9/1883 |
| DE | 1 150 965 | 7/1963 |
| DE | 24 53 529 | 5/1976 |
| FR | 1320250 | 3/1963 |
| FR | 2208398 | 6/1974 |
| GB | 933680 | * 8/1963 |

* cited by examiner

*Primary Examiner*—J. Parsa
(74) *Attorney, Agent, or Firm*—Joseph C. Gil; John E. Mrozinski, Jr.

(57) ABSTRACT

The invention is directed to a process for the production of 1,5-dinitronaphthalene wherein naphthalene is nitrated by nitric acid in the absence of sulfuric acid at temperatures of from 30 to 80° C., wherein the nitric acid has a concentration of from 72 to 87 wt.-%, the reaction mixture obtained is filtered at temperatures of from 5 to 20° C. and the solid precipitate obtained is washed with water, and 1,5-dinitronaphthalene is isolated from the washed precipitate by washing with acetone.

7 Claims, No Drawings

PROCESS FOR THE PRODUCTION OF 1,5-DINITRONAPHTHALENE

FIELD OF THE INVENTION

The invention is directed to a process for the production of 1,5-dinitronaphthalene (1,5-DNN) based on the direct nitration of naphthalene.

BACKGROUND OF THE INVENTION 1,5-dinitronaphthalene is an intermediate in the production of 1,5-diaminonaphthalene, naphthalenediisocyanate-1,5 and various condensation polymers.

In practice, a crude mixture comprising 1,5-dinitronaphthalene, 1,8-dinitronaphthalene, 1-mononitronaphthalene and products of partial oxidation may be prepared by nitration of naphthalene with mixtures of sulfuric and nitric acid (DE-A-11 50 965).

But, the use of mixtures of sulfuric acid and nitric acid in the production of crude mixtures of dinitronaphthalenes creates a need for the setting up of expensive and ecologically hazardous units for processing of used acids and separate recovery of nitric and sulfuric acids.

There are a number of publications which deal with increasing the yield in 1,5-dinitronaphthalene production by the introduction of reagents and solvents into the nitrating mixtures (U.S. Pat. No. 3,221,062, DE-A-24 53 529, FR-A-22 08 398, DD-A-26541).

But, it is much more advantageous to use nitric acid as a single nitrating agent in practice in order to avoid expensive separation and recovery processes.

From U.S. Pat. No. 3,998,893 a process for the production of a crude dinitronaphthalene mixture using nitric acid is known. But mononitronaphthalene is used as a primary raw material in the process according to U.S. Pat. No. 3,998,893. In addition, U.S. Pat. No. 3,998,893 does not provide any information about the isomeric composition of the produced crude dinitronaphthalene mixture, about the yield of 1,5 dinitronaphthalene and about its separation from the crude dinitronaphthalene mixture.

The separation and purification of 1,5-dinitronaphthalene from the crude dinitronaphthalene mixture is an important process step in the production of 1,5-dinitronaphthalene. But, no simple method for the separation and purification is known from the literature. In FR-A-13 20 250, the use of dimethylformamide (DMFA) as a selective solvent-extractant for the separation of 1,5-dinitronaphthalene is disclosed.

But, the technological complexity of dimethylformamide (DMFA) recovery and relatively considerable residual solubility of 1,5-dinitronaphthalene in the extractant render this method unsuitable for a practical implementation.

SUMMARY OF THE INVENTION

Accordingly, the present invention reduces or eliminates problems inherent in the art by providing a simple process for the production of 1,5-dinitronaphthalene.

This and other advantages and benefits of the present invention will be apparent from the Detailed Description of the Invention herein below.

DETAILED DESCRIPTION OF THE INVENTION

The present invention will now be described for purposes of illustration and not limitation. Except in the operating examples, or where otherwise indicated, all numbers expressing quantities, percentages and so forth in the specification are to be understood as being modified in all instances by the term "about." The present invention is directed to a process for the production of 1,5-dinitronaphthalene involving nitrating naphthalene with nitric acid in the absence of sulfuric acid at temperatures of from 30–80° C., wherein the nitric acid has a concentration of from 72 to 87 wt.-%, and filtering the nitrated naphthalene at temperatures of from 5 to 20° C. and washing the solid precipitate obtained with water, and isolating 1,5-dinitronaphthalene from the washed precipitate by washing with acetone.

The process for the production of 1,5-dinitronaphthalene according to the invention is based on the direct nitration of naphthalene by nitric acid having a concentration of 72–87 wt.-% without mononitronaphthalene isolation. The washing of the reaction products with water and acetone leads to 1,5-dinitronaphthalene of high purity [$\geq$98 wt.-%]. The acetone and nitric acid used in the process may be recovered and returned into the process. 1,8-dinitronaphthalene is produced in the process as a by-product.

The nitration step may be performed as follows: Nitric acid of 72–87 wt.-% is charged into a reactor and powdered naphthalene is dosed by stirring. The nitration reaction is performed at a temperature of from 30 to 80° C., preferably of from 45 to 65° C. The time period of naphthalene nitration is preferably in the range of from 15 minutes to 2 hours, more preferably of from 1.5 to 2 hours, depending on the concentration of primary nitric acid, the intensity of cooling, the temperature in the reactor and the molar ratio of the reactants.

The molar ratio of nitric acid to naphthalene is preferably at least 8:1, more preferably in the range of from 8 to 20:1.

The nitration process may be performed in batch and continuous reactors.

Dinitronaphthalene isomers are of limited solubility in used nitric acid. In order to reduce losses in the washing step, upon completion of the nitration, the reaction mixture is cooled to reduce the solubility of the dinitronaphthalene isomers in the used nitric acid and then filtered at 5 to 20° C. The solid precipitate obtained is then washed by water preferably up to the neutral reaction. In a preferred embodiment of the invention the reaction mixture is cooled and filtered at 5 to 20° C., and the solid precipitate obtained is then washed by returned nitric acid having a preferred concentration of from 65 to 70 wt.-% and then washed by water up to the neutral reaction.

In the final step of the inventive process, the washed crude precipitate obtained is treated with acetone to extract the 1,8-dinitronaphthalene isomer and other impurities. The extraction may be preferably carried out by stirring the crude mixture in acetone. The temperature of the extraction is preferably in the range of from 45 to 55° C., more preferably of from 50 to 55° C. The extraction may be performed for 5–30 minutes, preferably for 15 to 20 minutes followed by cooling of the suspension to 15 to 20° C. and its filtration. The precipitate is then preferably washed on a filter with pure cooled acetone, then washed with water and dried at a temperature of from 20° C. to 110° C., preferably of from 100 to 110° C.

In the extraction step, preferably 3 to 7 kg of acetone, more preferably 4 to 6 kg of acetone per 1 kg of dry crude dinitronaphthalene mixture are used to extract the undesired substances accompanying the isomer 1,5-dinitronaphthalene.

After the extraction has been performed, two thirds of the solvent acetone may be distilled off and the residue (bottom product) may be cooled down to 10 to 20° C. The isomer 1,8 dinitronaphthalene, usually 5–10% by weight of impurities, may then be crystallized from the bottom product. After the crystal precipitates (mainly 1,8-dinitronaphthalene) have been separated by filtering, the mother liquors may be combined with the main extracts. Condensed acetone is preferably returned to the extraction stage. The 1,8-dinitronaphthalene is usually washed with water and dried at 20–105° C. Wash solutions containing water and acetone may be rectified whereby the acetone may be returned to the cycle.

Used nitric acid can be returned to the nitration stage after pre-concentration by addition of 95 to 99.9 wt.-% nitric acid, preferably 98–99 wt.-% nitric acid.

EXAMPLES

A. Naphthalene Nitration

Nitric acid was placed in a 250 ml three-necked round-bottomed flask equipped with a paddle mixer, a thermometer, a cone funnel. A weighed portion of finely pulverized naphthalene was added by stirring at room temperature. The reaction mixture was self-heated to 50° C. with first naphthalene portions. Further naphthalene dosing rate was maintained so that the temperature in the reactor maintained from 30 to 40° C.; to do this, the flask was cooled by cold water. After completing the dosing of naphthalene (15–25 minutes), the reaction mixture was stirred at 45- to 65° C. for 2 hours. The reaction mixture was cooled to 15° C. and the precipitate was filtered in a glass filter. The precipitate was washed four times with cooled nitric acid (65%), 7 ml each time. After careful squeezing, the precipitate was washed by water to the neutral reaction of wash waters. The washed precipitate was dried in the open and weighed. The composition of crystal products of the nitration was analyzed by GLC (Gas Liquid Chromatography) in HP-6840.

The amounts and concentrations of the reagents used in Examples 1 to 9 are given in Table 1.

B. Separation of Dinitronaphthalene Isomers

Each of the crude mixtures of dinitronaphthalenes obtained in Examples 1 to 9 was placed together with 200 ml of acetone in a 500 ml flask equipped with a mixer. The suspension was heated at 50- to 55° C. for 15 minutes. The suspension was then cooled to 15° C. by stirring and filtered in a vacuum filter. The precipitate was then washed with 20 ml of acetone three times in the filter, then with water three times and dried in the open at room temperature.

The dry product was weighed, content of basic substance was analyzed by GLC. The data and results of the Examples 1 to 9 are given in Table 1.

TABLE 1

| Number of example | Naphthalene ($C_{10}H_8$) | | Nitric Acid | | | Molar ratio $HNO_3$: $C_{10}H_8$ | Amount of crude DNN (g) | Composition of crude DNN (%, HP GLC analysis) | | | Amount of extracted 1,5-DNN (g) | Content of 1,5-DNN (%, HP GLC analysis) | Yield of 1,5-DNN (wt.-%) |
|---|---|---|---|---|---|---|---|---|---|---|---|---|---|
| | g | mole | ml/g | Conc., (wt.-%) | Moles | | | 1,5-DNN | 1,8-DNN | Other | | | |
| 1: | 25 | 0.195 | 150/221 | 87 | 3.055 | 15.7 | 38.3 | 38.3 | 57.8 | 3.9 | 14.7 | 98.3 | 34.6 |
| 2: | 25 | 0.195 | 155/226 | 82 | 3.59 | 15.1 | 39.5 | 39.3 | 57.5 | 3.2 | 15.5 | 99.0 | 36.5 |
| 3: | 20 | 0.155 | 160/231 | 78 | 2.86 | 18.5 | 30.7 | 37.6 | 58.7 | 3.7 | 11.5 | 97.5 | 33.8 |
| 4: | 20 | 0.155 | 170/241 | 72 | 2.76 | 17.8 | 31.5 | 38.5 | 57.2 | 4.3 | 12.1 | 98.8 | 35.6 |
| 5: | 40 | 0.31 | 150/221 | 87 | 3.055 | 9.9 | 62.7 | 36.9 | 58.6 | 4.5 | 23.0 | 98.5 | 33.8 |
| 6: | 40 | 0.31 | 155/226 | 82 | 3.59 | 11.6 | 63.1 | 38.7 | 58.0 | 3.3 | 24.2 | 99.1 | 35.6 |
| 7: | 30 | 0.234 | 120/170 | 72 | 1.95 | 8.3 | 48.1 | 39.5 | 57.3 | 3.2 | 18.8 | 98.5 | 36.9 |
| 8: | 30 | 0.234 | 95/140 | 87 | 1.93 | 8.3 | 47.4 | 37.6 | 58.6 | 3.8 | 17.9 | 97.9 | 35.1 |
| 9: | 30 | 0.234 | 105/152 | 78 | 1.88 | 8.0 | 47.6 | 39.2 | 56.5 | 4.3 | 18.2 | 98.7 | 35.7 |

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A process for the production of 1,5-dinitronaphthalene comprising:

nitrating naphthalene with nitric acid in the absence of sulfuric acid at a temperature of from about 30° C. to about 80° C., wherein the nitric acid has a concentration of from about 72 wt.-% to about 87 wt.-%;

filtering the nitrated naphthalene at a temperature of from about 5° C. to about 20° C. and washing solid precipitate obtained with water; and isolating 1,5-dinitronaphthalene from the washed precipitate by washing with acetone.

2. The process according to claim 1, wherein the molar ratio of nitric acid to naphthalene used in the nitration is at least about 8:1.

3. The process according to claim 1, wherein nitric acid which has been used in the nitration step is mixed with fresh nitric acid of from 95 to 99 wt.-% to produce a mixed nitric acid of from 72 to 87 wt.-% and is used in a subsequent nitration step.

4. The process according to claim 1, wherein the ratio of washed precipitate to acetone is in the range of from about 1:3 to about 1:7 by weight.

5. The process according to claim 1, further including evaporating and returning the acetone which contains 1,8-dinitronaphthalene to the step of isolating.

6. The process according to claim 1, wherein the step of nitrating occurs at a temperature of from about 45° C. to about 65° C.

7. In a process of making one of 1,5-diaminonaphthalene and 1.5-diisocyanatenaphthalene, the improvement comprising including 1,5-dinitronaphthalene made by the process according to claim 1.

* * * * *